United States Patent
Kuechler et al.

(10) Patent No.: US 9,340,474 B2
(45) Date of Patent: May 17, 2016

(54) PROCESS FOR PRODUCING PHENOL

(71) Applicant: ExxonMobil Chemical Patents Inc., Baytown, TX (US)

(72) Inventors: Keith H. Kuechler, Friendswood, TX (US); Jason D. Davis, Humble, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/439,154

(22) PCT Filed: Nov. 22, 2013

(86) PCT No.: PCT/US2013/071420
§ 371 (c)(1),
(2) Date: Apr. 28, 2015

(87) PCT Pub. No.: WO2014/088841
PCT Pub. Date: Jun. 12, 2014

(65) Prior Publication Data
US 2015/0291493 A1  Oct. 15, 2015

Related U.S. Application Data

(60) Provisional application No. 61/734,202, filed on Dec. 6, 2012, provisional application No. 61/734,213, filed on Dec. 6, 2012, provisional application No. 61/735,655, filed on Dec. 11, 2012.

(30) Foreign Application Priority Data

Feb. 11, 2013  (EP) ..................................... 13154756

(51) Int. Cl.
| | | |
|---|---|---|
| C07C 45/53 | (2006.01) | |
| C07C 37/08 | (2006.01) | |
| C07C 2/66 | (2006.01) | |
| C07C 29/48 | (2006.01) | |
| C07C 37/74 | (2006.01) | |
| C07C 2/74 | (2006.01) | |
| C07B 41/00 | (2006.01) | |
| C07C 45/28 | (2006.01) | |

(52) U.S. Cl.
CPC .................. *C07C 29/48* (2013.01); *C07B 41/00* (2013.01); *C07C 2/66* (2013.01); *C07C 2/74* (2013.01); *C07C 37/08* (2013.01); *C07C 37/74* (2013.01); *C07C 45/28* (2013.01); *C07C 45/53* (2013.01); C07C 2101/14 (2013.01); C07C 2523/06 (2013.01); C07C 2523/14 (2013.01); C07C 2523/44 (2013.01); C07C 2523/46 (2013.01); C07C 2523/75 (2013.01); C07C 2523/755 (2013.01); C07C 2529/70 (2013.01)

(58) Field of Classification Search
CPC ............ C07C 45/53; C07C 37/08; C07C 2/66
USPC .......................... 568/376, 798, 799; 585/467
See application file for complete search history.

(56) References Cited

U.S. PATENT DOCUMENTS

| | | |
|---|---|---|
| 3,049,447 A | 8/1962 | Knapp |
| 3,959,381 A | 5/1976 | Arkell et al. |
| 4,147,726 A | 4/1979 | Wu |
| 4,160,000 A | 7/1979 | Hutto et al. |
| 4,358,618 A | 11/1982 | Sifniades et al. |
| 6,037,513 A | 3/2000 | Chang et al. |
| 6,720,462 B2 | 4/2004 | Kuhnle et al. |
| 6,852,893 B2 | 2/2005 | Kuhnle et al. |
| 2002/0169331 A1 | 11/2002 | Miura et al. |
| 2011/0301387 A1 | 12/2011 | Wang et al. |

FOREIGN PATENT DOCUMENTS

| | | |
|---|---|---|
| CN | 1962574 | 5/2007 |
| EP | 1074536 | 2/2001 |
| WO | WO 2009/025939 | 2/2009 |
| WO | WO 2009/058527 | 5/2009 |
| WO | WO 2009/058531 | 5/2009 |
| WO | WO 2009/128984 | 10/2009 |
| WO | WO 2009/131769 | 10/2009 |
| WO | WO 2010/098916 | 9/2010 |
| WO | WO 2012/036822 | 3/2012 |
| WO | WO 2012/036826 | 3/2012 |
| WO | WO 2012/036827 | 3/2012 |
| WO | WO 2014/043188 | 3/2014 |
| WO | WO 2014/043478 | 3/2014 |
| WO | WO 2014/081597 | 5/2014 |
| WO | WO 2014/088841 | 6/2014 |
| WO | WO 2014/088842 | 6/2014 |

*Primary Examiner* — Sikarl Witherspoon
(74) *Attorney, Agent, or Firm* — Stephen A. Baehi; Siwen Chen

(57) ABSTRACT

In a process for producing phenol and/or cyclohexanone, a cleavage reaction mixture containing cyclohexyl-1-phenyl-hydroperoxide and cyclohexylbenzene is contacted with sulfuric acid and water under cleavage conditions effective to form a cleavage reaction effluent containing phenol, cyclohexanone, cyclohexylbenzene, water, sulfuric acid and 1-phenylcyclohexanol. At least a portion of the cleavage reaction effluent is neutralized with a basic material to produce a neutralized cleavage product and at least a portion of the neutralized cleavage product is supplied in the absence of an added dehydration catalyst to a distillation column. The distillation column is operated so that at least a portion of the neutralized cleavage product is exposed to a temperature greater than 70° C. at at least one location in the distillation column whereby at least a portion of the 1-phenylcyclohexanol in the neutralized cleavage product is dehydrated to phenylcyclohexene.

23 Claims, 1 Drawing Sheet

PROCESS FOR PRODUCING PHENOL

PRIORITY CLAIM TO RELATED APPLICATIONS

This application is a National Stage Application of International Application No. PCT/US2013/071420 filed Nov. 22, 2013, which claims priority to U.S. Provisional Application Ser. No. 61/734,202 filed Dec. 6, 2012; 61/734,213 filed Dec. 6, 2012; 61/735,655 filed Dec. 11, 2012; and European Application No. 13154756.4 filed Feb. 11, 2013, the disclosures of which are fully incorporated herein by their reference.

PRIORITY CLAIM TO RELATED APPLICATIONS

This application claims priority to U.S. Provisional Application Ser. Nos. 61/734,202 filed Dec. 6, 2012; 61/734,213 filed Dec. 6, 2012; 61/735,655 filed Dec. 11, 2012; and European Application No. 13154756.4 filed Feb. 11, 2013, the disclosures of which are fully incorporated herein by their reference.

FIELD

The present invention relates to a process for producing phenol.

BACKGROUND

Phenol is an important product in the chemical industry and is useful in, for example, the production of phenolic resins, bisphenol A, ε-caprolactam, adipic acid, and plasticizers.

Currently, the most common route for the production of phenol is the Hock process via cumene. This is a three-step process in which the first step involves alkylation of benzene with propylene in the presence of an acidic catalyst to produce cumene. The second step is oxidation, preferably aerobic oxidation, of the cumene to the corresponding cumene hydroperoxide. The third step is the cleavage of the cumene hydroperoxide in the presence of heterogeneous or homogenous catalysts into equimolar amounts of phenol and acetone, a co-product. However, the world demand for phenol is growing more rapidly than that for the acetone co-product. In addition, due to developing shortages in supply, the cost of propylene is likely to increase.

Thus, a process that avoids or reduces the use of propylene as a feed and coproduces higher ketones, rather than acetone, may be an attractive alternative route to the production of phenol. For example, there is a growing market for cyclohexanone, which is used as an industrial solvent, as an activator in oxidation reactions and in the production of adipic acid, cyclohexanone resins, cyclohexanone oxime, caprolactam, and nylon 6.

It is known that phenol and cyclohexanone can be co-produced by a variation of the Hock process in which cyclohexylbenzene is oxidized to obtain cyclohexylbenzene hydroperoxide and the hydroperoxide is decomposed in the presence of an acid catalyst to the desired phenol and cyclohexanone. Although various methods are available for the production of cyclohexylbenzene, a preferred route is via benzene hydroalkylation in which benzene is contacted with hydrogen in the presence of a catalyst such that a portion of the benzene is converted into cyclohexene which then reacts with the remaining benzene to produce the desired cyclohexylbenzene. One such method is disclosed in U.S. Pat. No. 6,037,513, in which the catalyst comprises a molecular sieve of the MCM-22 family and at least one hydrogenation metal selected from palladium, ruthenium, nickel, cobalt, and mixtures thereof. The '513 patent also discloses that the resultant cyclohexylbenzene can be oxidized to the corresponding hydroperoxide which is then decomposed to the desired phenol and cyclohexanone products in roughly equimolar amounts.

Several technical challenges not seen in the cumene-based Hock process exist in producing phenol via cyclohexylbenzene. One such challenge is that non-negligible amounts of by-products, including phenylcyclohexanols, are normally generated during the oxidation step. As exemplified in our U.S. Patent Application Publication No. 2011/0301387, by conducting the cleavage reaction in the presence of a high concentration of cyclohexylbenzene and/or a high concentration of sulfuric acid, it is possible to convert most, if not all, of the 1-phenylcyclohexanol, and even the less reactive 2-, 3- and 4-phenylcyclohexanols, to useful phenylcyclohexene during the cleavage reaction. The phenylcyclohexene may be subsequently hydrogenated and recycled as cyclohexylbenzene to the oxidation reaction to produce additional cyclohexylbenzene hydroperoxide.

SUMMARY

It has now been found that improved yields of the desired phenol and cyclohexanone products and lower processing costs can be achieved by conducting the cleavage reaction at milder conditions. Moreover, although these milder conditions tend to have low conversion of phenylcyclohexanols, it has also been found that at least some of the phenylcyclohexanol isomers can readily be dehydrated to phenylcyclohexene by proper control of the downstream neutralization and distillation steps involved in recovery of the phenol and cyclohexanone products. Accordingly, the present invention seeks to provide a process for producing phenol and cyclohexanone from cyclohexylbenzene in which the cleavage reaction is operated to maximize the yield of the desired products and at least a portion of the phenylcyclohexanol produced during the oxidation reaction is converted to phenylcyclohexene by thermal dehydration during downstream processing of the cleavage effluent.

In one aspect, the invention resides in a process for producing phenol and/or cyclohexanone, the process comprising:

(a) providing a cleavage reaction mixture containing cyclohexyl-1-phenyl-hydroperoxide and cyclohexylbenzene;

(b) contacting at least a portion of the cleavage reaction mixture with sulfuric acid and water under cleavage conditions effective to form a cleavage reaction effluent containing phenol, cyclohexanone, cyclohexylbenzene, water, sulfuric acid, and 1-phenylcyclohexanol;

(c) neutralizing at least a portion of the cleavage reaction effluent with a basic material to produce a neutralized cleavage product; and (d) supplying at least a portion of the neutralized cleavage product in the absence of an added dehydration catalyst to a distillation column which is operated so that at least a portion of the neutralized cleavage product is exposed to a temperature greater than 70° C. at at least one location in the distillation column whereby at least a portion of the 1-phenylcyclohexanol in the neutralized cleavage product is dehydrated to phenylcyclohexene.

In a further aspect, the invention resides in a process for producing phenol and/or cyclohexanone, the process comprising:

(a) providing a cleavage feed containing greater than 40 wt % and no greater than 95 wt % cyclohexyl-1-phenyl-hydroperoxide and at least 5.0 wt % and less than 60 wt % cyclohexylbenzene;

(b) mixing the cleavage feed with a cleavage recycle containing phenol, cyclohexanone, cyclohexylbenzene, water, and sulfuric acid, to produce a cleavage reaction mixture containing from 20 wt % to 50 wt % phenol, from 20 wt % to 50 wt % cyclohexanone, from 1.0 wt % to 10 wt % cyclohexyl-1-phenyl-hydroperoxide, from 5.0 wt % to 60 wt % cyclohexylbenzene, from 0.1 wt % to 4 wt % water, and from 10 wppm to 1000 wppm sulfuric acid;

(c) reacting at least a portion of the cleavage reaction mixture at a temperature from 30° C. to 70° C. for a time sufficient to convert at least 50% of the cyclohexyl-1-phenyl-hydroperoxide in the cleavage reaction mixture and produce a cleavage effluent containing phenol, cyclohexanone, cyclohexylbenzene, water, sulfuric acid, and 1-phenylcyclohexanol;

(d) dividing the cleavage reaction effluent into at least a cleavage product and the cleavage recycle;

(e) neutralizing at least a portion of the cleavage product with a basic material to produce a neutralized cleavage product; and (f) supplying at least a portion of the neutralized cleavage product in the absence of an added dehydration catalyst to a distillation column which is operated so that at least a portion of the neutralized cleavage product is exposed to a temperature greater than 70° C. at at least one location in the distillation column whereby at least a portion of the 1-phenylcyclohexanol in the neutralized cleavage product is dehydrated to phenylcyclohexene.

The weight ratio of the cleavage recycle product to the cleavage product can be, e.g., from 1:1 to 50:1, such as from 10:1 to 40:1.

The cleavage conditions include a temperature no greater than 70° C., such as from 30° C. to 70° C. Desirably, the temperature at said at least one location in the distillation column is from 80° C. to 120° C. The distillation column can be a dividing wall distillation column.

The process may further comprise the following additional steps:

(g) contacting cyclohexylbenzene with an oxygen-containing compound in the presence of a catalyst under conditions effective to produce an oxidation product comprising cyclohexyl-1-phenyl-hydroperoxide and at least 70 wt % unreacted cyclohexylbenzene; and (h) removing a portion of the unreacted cyclohexylbenzene from the oxidation product to provide the cleavage feed.

DETAILED DESCRIPTION OF THE EMBODIMENTS

Figure 1:
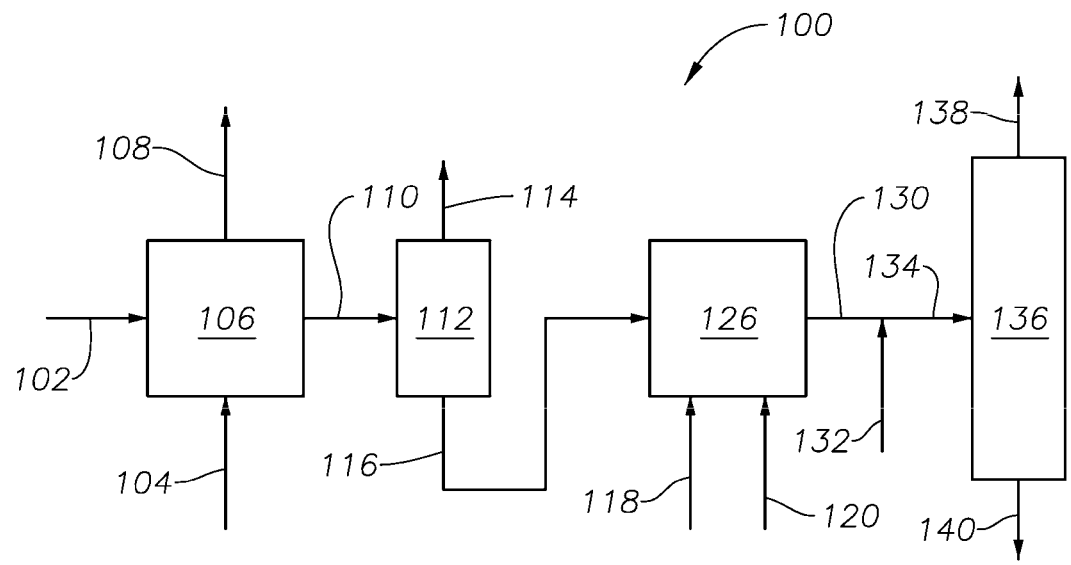
FIG. 1 is a flow diagram of a process for producing phenol and/or cyclohexanone according to a first example of the present application.

In the present disclosure, a process may be described as comprising of at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, some steps may be conducted simultaneously, for example, in the same reaction zone. Preferably, the steps are performed in the order listed.

Unless otherwise indicated, all numbers in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a hydrogenating metal" include embodiments where one, two or more hydrogenating metals are used, unless specified to the contrary or the context clearly indicates that only one hydrogenating metal is used. Likewise, "an oxygenated hydrocarbon" should be interpreted to include one or more types of hydrogenated hydrocarbon at various concentrations unless specified or indicated by the context to mean only one specific type of hydrogenated hydrocarbon.

As used herein, the term "cyclohexylbenzene" shall mean benzene substituted by a single cyclohexyl group, unless specified to the contrary or the context clearly indicates otherwise. As used herein, the generic term "dicyclohexylbenzene" shall include 1,2-dicyclohexylbenzene, 1,3-dicyclohexylbenzene, 1,4-dicyclohexylbenzene, and mixtures and combinations of at least two thereof in any proportion. As used herein, the generic term "tricyclohexylbenzene" shall include 1,2,3-tricyclohexylbenzene, 1,2,4-tricyclohexylbenzene and 1,3,5-tricyclohexylbenzene, and combinations and mixtures thereof at any proportion. The generic term "polycyclohexylbenzene" shall include any of the dicyclohexylbenzene isomers and tricyclohexylbenzene isomers described above, and combinations and mixtures of at least two thereof in any proportion.

Described herein is a process for producing phenol and/or cyclohexanone from cyclohexylbenzene. In this process, the cyclohexylbenzene is initially oxidized to produce cyclohexyl-1-phenyl-hydroperoxide, which is then contacted with a sulfuric acid cleavage catalyst under mild conditions effective to produce a cleavage effluent containing the desired phenol and cyclohexanone in high yield. However, the oxidation step also produces by-products, including 1-phenylcyclohexanol, which in the present process is thermally dehydrated (in the absence of a dehydration catalyst) to phenylcyclohexene for recycle back to the oxidation step. In particular, the cleavage effluent in initially neutralized with a base and then the neutralized effluent is supplied to a distillation column operating in excess of 70° C., such that at least a portion of the 1-phenylcyclohexanol in the neutralized cleavage product is converted to phenylcyclohexene.

Preferably, the process of the present disclosure forms a portion of an integrated process for producing phenol from benzene in which the benzene is initially alkylated or hydroalkylated to produce the cyclohexylbenzene feed to the present process. The ensuing description will therefore focus on this integrated process.

Production of Cyclohexylbenzene

The cyclohexylbenzene starting material for the present process can be produced by the alkylation of benzene with cyclohexene according to the following reaction:

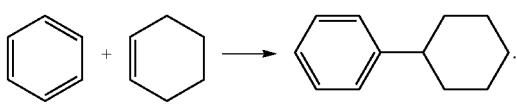

The cyclohexene can be supplied to the reaction zone as a separate feed from the benzene, but normally is produced in situ by the selective hydrogenation of benzene in the presence of a bifunctional catalyst. Such a reaction is generally termed "hydroalkylation" and may be summarized as follows:

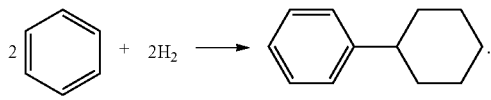

Any commercially available benzene feed can be used in the hydroalkylation step. Preferably, the benzene has a purity level of at least 99 wt %. Similarly, although the source of hydrogen is not critical, it is desirable that the hydrogen is at least 99 wt % pure.

Preferably, the total feed to the hydroalkylation step contains less than 1000 ppm, such as less than 500 ppm, for example less than 100 ppm, water. In addition, the total feed may contain less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but the hydrogen supply is desirably arranged such that the molar ratio of hydrogen to benzene in the hydroalkylation feed is from about 0.15:1 to about 15:1, such as from about 0.4:1 to about 4:1, for example from about 0.4:1 to about 0.9:1.

In addition to the benzene and hydrogen, a diluent, which is substantially inert under hydroalkylation conditions, may be supplied to the hydroalkylation reaction. The diluent may be a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, advantageously the diluent is added in an amount such that the weight ratio of the diluent to the aromatic compound is at least 1:100; for example at least 1:10, but no more than 10:1, for example no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are from about 100° C. to about 400° C., such as from about 125° C. to about 250° C., while suitable reaction pressures are from about 100 kPa to about 7,000 kPa, such as from about 500 kPa to about 5,000 kPa.

The catalyst employed in the hydroalkylation reaction is a bifunctional catalyst comprising a hydrogenating metal component and an alkylating solid acid component. Advantageously, the alkylating solid acid component comprises a molecular sieve of the MCM-22 family. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth Edition, 2001, the entire content of which is incorporated as reference);

molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07, and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), MCM-56 (described in U.S. Pat. No. 5,362,697), UZM-8 (described in U.S. Pat. No. 6,756,030), and mixtures thereof. Preferably, the molecular sieve is selected from (a) MCM-49; (b) MCM-56; and (c) isotypes of MCM-49 and MCM-56, such as ITQ-2.

Any known hydrogenating metal can be employed in the hydroalkylation catalyst, although suitable metals include palladium, ruthenium, nickel, zinc, tin, and cobalt, with palladium being particularly advantageous. Desirably, the amount of hydrogenating metal present in the catalyst is from about 0.05 wt % to about 10 wt %, such as from about 0.1 wt % to about 5.0 wt %, of the catalyst. Where the MCM-22 family molecular sieve is an aluminosilicate, the amount of hydrogenating metal present may be such that the molar ratio of the aluminum in the molecular sieve to the hydrogenating metal is from about 1.5 to about 1500, for example from about 75 to about 750, such as from about 100 to about 300.

The hydrogenating metal may be directly supported on the MCM-22 family molecular sieve by, for example, impregnation or ion exchange. Preferably, at least 50 wt %, for example at least 75 wt %, and desirably substantially all of the hydrogenating metal is supported on an inorganic oxide separate from but composited with the molecular sieve. In particular, it is found that by supporting the hydrogenating metal on the inorganic oxide, the activity of the catalyst and its selectivity to cyclohexylbenzene and dicyclohexylbenzene are increased as compared with an equivalent catalyst in which the hydrogenating metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenating metal is deposited on the inorganic oxide by, e.g., impregnation, before the metal-containing inorganic oxide is composited with the molecular sieve. For example, the catalyst composite can be produced by co-pelletization, in which a mixture of the molecular sieve and the metal-containing inorganic oxide are formed into pellets at high pressure (desirably about 350 kPa to about 350,000 kPa), or by co-extrusion, in which a slurry of the molecular sieve and the metal-containing inorganic oxide, optionally together with a separate binder, are forced through a die. If necessary, additional hydrogenating metal can subsequently be deposited on the resultant catalyst composite.

Although the hydroalkylation reaction using an MCM-22 family zeolite catalyst is highly selective towards cyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired monoalkylated species.

Transalkylation with additional benzene may be conducted in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is desirably conducted under at least partial liquid phase conditions, which suitably include a temperature of about 100° C. to about 300° C., a pressure of about 800 kPa to about 3500 kPa, a weight hourly space velocity of about 1 $hr^{-1}$ to about 10 $hr^{-1}$ on total feed, and a benzene/dicyclohexylbenzene weight ratio about of 1:1 to about 5:1.

Dealkylation or cracking may also be effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia, and mixtures thereof. Desirably, the acid catalyst includes at least one aluminosilicate, aluminophosphate or silicoaluminophosphate of the FAU, AEL, AFI, and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is desirably from 0 to about 0.9, such as from about 0.01 to about 0.5. Similarly, although the dealkylation reaction can be conducted in the absence of added hydrogen, hydrogen is advantageously introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the $C_6$-rich stream can be recycled to the hydroalkylation reactor to provide not only a portion of the benzene feed but also a portion of the diluents mentioned above.

In some cases, it may be desirable to supply some of the $C_6$-rich stream to a dehydrogenation reaction zone, where the $C_6$-rich stream is contacted with a dehydrogenation catalyst under dehydrogenation conditions sufficient to convert at least a portion of the cyclohexane in the $C_6$-rich stream portion to benzene, which again can be recycled to the hydroalkylation reaction. The dehydrogenation catalyst desirably comprises (a) a support; (b) a hydrogenation-dehydrogenation component; and (c) an inorganic promoter. The support (a) may be selected from the group consisting of silica, a silicate, an aluminosilicate, zirconia, carbon nanotubes, and preferably comprises silica. Suitable hydrogenation-dehydrogenation components (b) comprise of at least one metal selected from Groups 6 to 10 of the Periodic Table of Elements, such as platinum, palladium and compounds, and mixtures thereof. Desirably, the hydrogenation-dehydrogenation component is present in an amount from about 0.1 wt % to about 10 wt % of the catalyst. A suitable inorganic promoter (c) comprises at least one metal or compound thereof selected from Group 1 of the Periodic Table of Elements, such as a potassium compound. The promoter may be present in an amount from about 0.1 wt % to about 5.0 wt % of the catalyst. Suitable dehydrogenation conditions include a temperature of about 250° C. to about 500° C., a pressure of about atmospheric to about 500 psig (100 kPa to 3550 kPa), a weight hourly space velocity of about 0.2 $hr^{-1}$ to 50 $hr^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene (3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the $C_{12}$ stream. Similarly, bicyclohexyl (BCH) can lead to separation problems downstream. Thus, at least a portion of the hydroalkylation reaction product may be treated with a catalyst under conditions to remove at least 1,1-methylcyclopentylbenzene and/or bicyclohexyl from the product. The catalyst may be an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene (3-MCPB). The bicyclohexyl is believed to react with benzene present in the hydroalkylation reaction product to produce cyclohexane and more of the desired cyclohexylbenzene according to the following reaction:

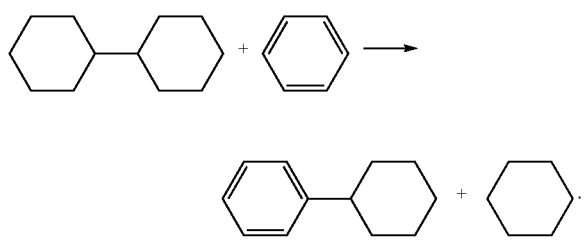

The catalytic treatment can be conducted on the direct product of the hydroalkylation reaction or after distillation of the hydroalkylation reaction product to separate the $C_6$ and/or the heavies fraction.

The cyclohexylbenzene product from the hydroalkylation reaction and any downstream reaction to remove the impurities discussed herein is separated from the reaction effluent(s) and is fed to the oxidation reaction described in more detail below.

Cyclohexylbenzene Oxidation

In order to convert the cyclohexylbenzene into phenol and cyclohexanone, the cyclohexylbenzene is initially oxidized to cyclohexyl-1-phenyl-hydroperoxide. This is accomplished by contacting the cyclohexylbenzene with an oxygen-containing gas, such as air and various derivatives of air. For example, it is possible to use air that has been compressed and filtered to removed particulates, air that has been compressed and cooled to condense and remove water, or air that has been enriched in oxygen above the natural approximately 21 mol % in air through membrane enrichment of air, cryogenic separation of air, or other conventional means.

The oxidation step can be conducted autogeneously, or more preferably, in the presence of a catalyst. Although any catalyst can be employed, a preferred oxidation catalyst includes an N-hydroxy substituted cyclic imide described in U.S. Pat. No. 6,720,462, which is incorporated herein by reference in its entirety for this purpose. For example, N-hydroxyphthalimide (NHPI), 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy (pyromellitic diimide), N,N'-dihydroxy(benzophenone-3,3', 4,4'-tetracarboxylic diimide), N-hydroxymaleimide, pyridine-2,3-dicarboximide, N-hydroxysuccinimide, N-hydroxy (tartaric imide), N-hydroxy-5-norbornene-2,3-dicarboximide, exo-N-hydroxy-7-oxabicyclo[2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, or N-hydroxy-o-benzenedisulphonimide may be used. For example, the catalyst can be N-hydroxyphthalimide. Another suitable catalyst is N,N',N"-trihydroxyisocyanuric acid. Each of the above cyclic imide catalysts contain the heteroatom nitrogen.

These oxidation catalysts can be used either alone or in conjunction with a free radical initiator, and further can be used as liquid-phase, homogeneous catalysts or can be supported on a solid carrier to provide a heterogeneous catalyst. Desirably, the N-hydroxy substituted cyclic imide or the N,N',N"-trihydroxyisocyanuric acid is employed in an amount from 0.0001 wt % to 15 wt %, such as from 0.001 wt % to 5.0 wt %, of the cyclohexylbenzene.

Suitable conditions for the oxidation step include a temperature from about 70° C. to about 200° C., such as about 90° C. to about 130° C., and a pressure of about 50 kPa to 10,000 kPa. A basic buffering agent may be added to react with acidic by-products that may form during the oxidation. In addition, an aqueous phase may be introduced. The reaction can take place in a batch or continuous flow fashion.

The reactor used for the oxidation reaction may be any type of reactor that allows for introduction of oxygen to and contacting of oxygen with cyclohexylbenzene. For example, the oxidation reactor may comprise a simple, largely open vessel with a distributor inlet for the oxygen-containing stream. For example, the oxidation reactor may have means to withdraw and pump a portion of its contents through a suitable cooling device and return the cooled portion to the reactor, thereby managing the exothermicity of the oxidation reaction. Alternatively, cooling coils providing indirect cooling, say by cooling water, may be operated within the oxidation reactor to remove the generated heat. Alternatively, the oxidation reactor may comprise a plurality of reactors in series, each conducting a portion of the oxidation reaction, optionally operating at different conditions selected to enhance the oxidation reaction at the pertinent conversion range of cyclohexylbenzene or oxygen, or both, in each. The oxidation reactor may be operated in a batch, semi-batch, or continuous flow manner.

Desirably, the product of the cyclohexylbenzene oxidation reaction contains at least 5.0 wt %, such as at least 10 wt %, for example from 10 wt % to 30 wt % cyclohexyl-1-phenyl-1-hydroperoxide based upon the total weight of the oxidation reaction effluent. Desirably, the oxidation reaction effluent contains no greater than 80 wt %, or no greater than 60 wt %, or no greater than 40 wt %, or no greater than 30 wt %, or no greater than 25 wt % of cyclohexyl-1-phenyl-1-hydroperoxide based upon the total weight of the oxidation reaction effluent. The oxidation reaction effluent may further comprise imide catalyst and unreacted cyclohexylbenzene. For example, the oxidation reaction effluent may include unreacted cyclohexylbenzene in an amount of at least 50 wt %, or at least 60 wt %, or at least 65 wt %, or at least 70 wt %, or at least 80 wt %, or at least 90 wt %, based upon total weight of the oxidation reaction effluent.

In addition to the desired cyclohexyl-1-phenyl-1-hydroperoxide (formula (F-I) below), the oxidation step tends to produce certain by-products which, if not removed and/or converted to useful materials would result in loss of valuable feed and/or could adversely influence downstream processes. Among these by-products are isomers of cyclohexyl-1-phenyl-1-hydroperoxide, including cyclohexyl-1-phenyl-2-hydroperoxide (formula (F-II) below), cyclohexyl-1-phenyl-3-hydroperoxide (formula (F-III) below), and cyclohexyl-1-phenyl-4-hydroperoxide (formula (F-IV) below). Other potential by-products are isomers of phenylcyclohexanol and phenylcyclohexanone, which may be generated in small amounts during the oxidation step but are mostly produced from the secondary isomers of cyclohexyl-1-phenyl-1-hydroperoxide during the subsequent cleavage step. Potential isomers of phenylcyclohexanol from either the oxidation or cleavage step include 1-phenyl-1-cyclohexanol (formula (F-V) below), 2-phenyl-1-cyclohexanol (formula (F-VI) below), 3-phenyl-1-cyclohexanol (formula (F-VII) below) and 4-phenyl-1-cyclohexanol (formula (F-VIII) below), and of phenylcyclohexanone from either the oxidation or cleavage step include 2-phenyl-1-cyclohexanone (formula (F-IX) below), 3-phenyl-1-cyclohexanone (formula (F-X) below) and 4-phenyl-1-cyclohexanone (formula (F-XI) below).

(F-I)
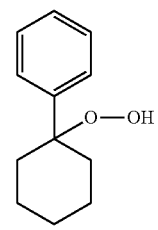

(F-II)
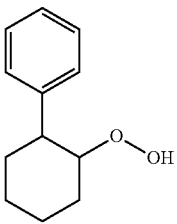

(F-III)
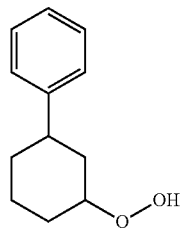

(F-IV)
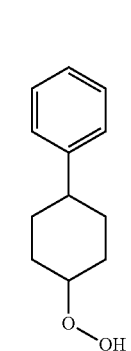

(F-V)
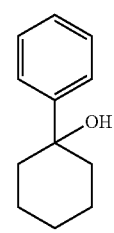

(F-VI)
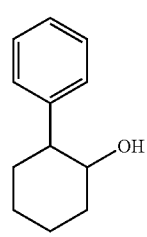

-continued (F-VII)
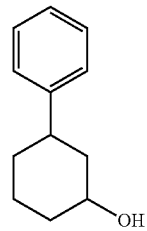

(F-VIII)
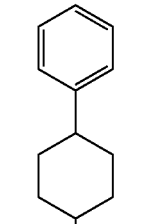

(F-IX)
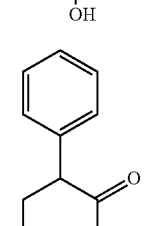

(F-X)
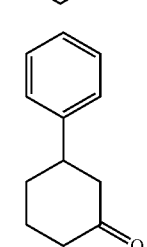

(F-XI)
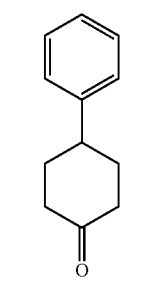

The phenylcyclohexanols may be present in the oxidation reaction effluent, or in the cleavage effluent, or a neutralized product thereof in an amount from 0.1 wt % to 10 wt % of the given effluent and the phenylcyclohexanones are present in an amount from 0.1 wt % to 5.0 wt % of the given effluent. In the present process, these by-products are removed and desirably converted to useful cyclohexylbenzene, which can then be recycled to the oxidation step. As explained below, removal and conversion of these by-products is desirably conducted after the cleavage step.

The oxidation reaction effluent will also contain some of the cyclic imide catalyst discussed above and, since the catalyst is expensive and can act as a poison to downstream reactions, it is desirable to remove and/or recover at least a portion of the catalyst from the oxidation reaction effluent for recycle back to the oxidation step. Removal of the cyclic imide may comprise a step of contacting the oxidation reaction effluent with an aqueous solution of a base, particularly a weak base having a pKb value greater than or equal to the pKa of the cyclic imide of the first catalyst, whereby the imide is extracted into the aqueous phase, leaving an organic phase which comprises the oxidized hydrocarbon product and a reduced level of cyclic imide. Alternatively, treatment of the oxidation effluent to remove at least a portion of the cyclic imide comprises contacting the effluent with an effective solid sorbent, such as a metal oxide or a metal carbonate and/or hydrogen carbonate. However, irrespective of the method used to treat the oxidation reaction effluent, the feed to the cleavage reaction will generally contain up to 2500 ppm by weight, such as up to 1500 ppm by weight, of heteroatom-containing compounds from the cyclic imide catalyst.

Hydroperoxide Cleavage

The final reactive step in the conversion of the cyclohexylbenzene into phenol and cyclohexanone involves the sulfuric acid-catalyzed cleavage of the cyclohexyl-1-phenyl-1-hydroperoxide produced in the oxidation step. Other hydroperoxides that may be present in the oxidation effluent stream may also undergo acid-catalyzed cleavage along with the desired cyclohexyl-1-phenyl-1-hydroperoxide. Typically, however, little or no conversion of any phenylcyclohexanol and phenylcyclohexanone produced in the oxidation reaction occurs during the cleavage step of the present process. In fact, additional production of phenylcyclohexanol and phenylcyclohexanone isomers can result from the cleavage process.

The feed to the cleavage step comprises some or all of the effluent from the oxidation reaction, desirably after removal of any remaining oxidation catalyst. It may also be desirable to concentrate the cyclohexyl-1-phenyl-1-hydroperoxide, by removing a portion of the unreacted cyclohexylbenzene, before the oxidation reaction effluent is supplied to the cleavage reaction. This may be achieved by a single or multi-stage distillation step at a pressure from 1 to 10 torr and a temperature from 80° C. to 120° C. For example, the oxidation reaction effluent may be concentrated so as to produce a cleavage feed containing greater than 40 wt % and no greater than 95 wt % cyclohexyl-1-phenyl-1-hydroperoxide and at least 5.0 wt % and less than 60 wt % cyclohexylbenzene.

The cleavage feed is then contacted with an aqueous sulfuric acid solution under cleavage conditions effective to convert the cyclohexyl-1-phenyl-1-hydroperoxide to phenol and cyclohexanone. For example, the process is conducted under relatively mild conditions so as to maximize the selectivity to these desired products. Such conditions include a temperature no greater than 70° C., such as from 30° C. to 70° C., and a pressure of at least 1 atmosphere for a time sufficient to convert at least 50% of the cyclohexyl-1-phenyl-1-hydroperoxide in the cleavage reaction mixture and produce a cleavage effluent containing phenol, cyclohexanone, cyclohexylbenzene, water, sulfuric acid, and some 1-phenylcyclohexanol.

The reactor used to effect the cleavage reaction may be any type of reactor known to those skilled in the art. For example, the cleavage reactor may be a simple, largely open vessel operating in a near-continuous stirred tank reactor mode, or a simple, open length of pipe operating in a near-plug flow reactor mode. Alternatively, the cleavage reactor may comprise a plurality of reactors in series, each performing a portion of the conversion reaction, optionally operating in different modes and at different conditions selected to enhance the cleavage reaction at the pertinent conversion range.

The cleavage reactor may be operable to transport a portion of the contents through a cooling device and return the cooled portion to the cleavage reactor, thereby managing the exothermicity of the cleavage reaction. Alternatively, the reactor may be operated adiabatically. Cooling coils operating within the cleavage reactor(s) may be used to remove at least part of the heat generated.

The entire cleavage effluent may be transported from the cleavage reactor to further downstream processing. Alternatively, the cleavage effluent is initially divided into at least two full boiling range aliquots, a cleavage product and a cleavage recycle. The cleavage product is removed for further downstream processing, while the cleavage recycle is mixed with the cleavage feed so that reaction mixture present in the cleavage reactor contains from 20 wt % to 50 wt % phenol, from 20 wt % to 50 wt % cyclohexanone, from 1.0 wt % to 10 wt % cyclohexyl-1-phenyl-hydroperoxide, from 5.0 wt % to 60 wt % cyclohexylbenzene, from 0.1 wt % to 4 wt % water, and from 10 wppm to 1000 wppm sulfuric acid. Desirably, the weight ratio of the cleavage recycle to the cleavage product is at least 1:1, for example at least 10:1, such as at least 20:1 but normally no greater than 50:1, for example no greater than 40:1, such as no greater than 30:1.

Treatment of the Cleavage Reaction Effluent

After removal of the cleavage recycle stream, the remaining cleavage product is initially treated with one or more basic compounds, such as amines or diamines, for example 2-methylpentane-1,5 diamine, to neutralize the residual sulfuric acid in the cleavage product. The resultant neutralized cleavage product may contain no more than 150 ppm by weight of sulfuric acid and no more than 150 ppm by weight of basic compounds.

The neutralized cleavage product is then fed, without the addition of a catalyst, to at least one distillation column operating at a temperature of greater than 70° C. whereby at least a portion of the 1-phenylcyclohexanol in the neutralized cleavage product is thermally dehydrated to phenylcyclohexene. The distillation column is also designed to separate the neutralized cleavage product into an overhead stream rich in phenol, cyclohexanone and components of a lower volatility than phenol and a bottoms stream rich in cyclohexylbenzene, phenylcyclohexene, phenylcyclohexanols, if any, and components of lower volatility than phenylcyclohexanols. The overhead stream may contain no more than 5.0 wt %, such as no more than 2.0 wt %, for example no more than 0.1 wt % cyclohexylbenzene, whereas the bottoms stream comprises no greater than 1.0 wt %, or no greater than 0.1 wt %, or even no greater than 100 wppm of water, pentanal, hexanal, methylcyclopentanone, cyclohexanone, and phenol combined.

A convenient form of distillation column is a dividing wall column. Dividing wall columns are known in the art, e.g., as described in O. Yildirim, et al., "Dividing Wall Columns in Chemical Process Industry: A Review on Current Activities", Separation and Purification Technology, Vol. 80, (2011), pp. 403-417, the entire contents of which are incorporated herein by reference.

The bottoms stream from the distillation column, which is rich in cyclohexylbenzene and phenylcyclohexene, may be recycled directly to the oxidation reaction, although levels of phenylcyclohexene above 1000 ppm by weight may be detrimental to the generation of the free radicals involved in the oxidation process. Therefore, the dehydration product may be hydrogenated to convert the phenylcyclohexene to cyclohexylbenzene before the product is recycled to oxidation. The hydrogenation may be effected by contacting the phenylcyclohexene-containing product with hydrogen in a hydrogenation reaction zone, which is advantageously operated at a temperature of 80° C. to 150° C., such as 80° C. to 120° C., and a hydrogen partial pressure of 15 kPa to 1000 kPa, such as 15 kPa to 300 kPa. The hydrogenation is desirably conducted in the presence of a catalyst comprising of at least one metal selected from Groups 6 to 12 of the Periodic Table of Elements, preferably palladium, on an inorganic support, such as silica.

The overhead stream from the distillation column, which is rich in phenol and cyclohexanone, can now undergo further conventional treatment steps to separate, purify and recover the phenol and cyclohexanone.

The invention will now be more particularly described with reference to the accompanying drawings.

FIG. 1 is a flow diagram of a process for producing phenol and/or cyclohexanone according to a first example of the present application, in which a feedstock comprising cyclohexylbenzene is provided by line 102 to an oxidation reactor 106. A stream comprising oxygen, conveniently air, is also provided to the oxidation reactor 106 by way of line 104. Conditions within oxidation reactor 106 are such that cyclohexylbenzene in the feedstock is oxidized to form cyclohexylbenzene hydroperoxide. An oxidation catalyst, such as the heteroatom containing-compound N-hydroxyphthalimde (NHPI), may be also introduced to oxidation reactor 106, by means not shown in FIG. 1, to facilitate the oxidation reaction.

As the oxidation reaction continues, oxygen is depleted and an oxygen depleted stream in line 108 is removed from oxidation reactor 106. When the oxidation reaction is conducted at or near atmospheric pressure, the oxygen depleted stream in line 108 may also contain lower volatility byproducts of the oxidation reaction, such as water, along with minor amounts of cyclohexylbenzene. In an operation not shown in FIG. 1, the oxygen depleted stream in line 108 may be further processed to recover the cyclohexylbenzene, remove water, and otherwise make the cyclohexylbenzene suitable for recycle to the oxidation reactor 106, and make other streams suitable for other uses or disposal.

An oxidation reaction product including cyclohexylbenzene hydroperoxide, desirably rich in cyclohexyl-1-phenyl-1-hydroperoxide but potentially including other hydroperoxides and dihydroperoxides, and optionally comprising phenylcyclohexanols, is withdrawn from oxidation reactor 106 by way of line 110. Where NHPI is introduced to the oxidation reactor 106, the oxidation reaction product may also contain NHPI.

The oxidation reaction product is provided to a separation device, for example, concentrator 112, which may be a type of thin film evaporator which is operated at very low pressure, e.g., from about 2 to about 5 torr, and a temperature of about 90° C. to about 120° C., so as to remove a first overhead product rich in cyclohexylbenzene. The first overhead product is removed from concentrator 112 in line 114 and, in addition to cyclohexylbenzene, is rich in components of a lower volatility than cyclohexylbenzene, and contains a very low amount of cyclohexylbenzene hydroperoxide, e.g., no greater than 100 wppm, or even no detectable cyclohexyl-1-phenyl-1-hydroperoxide.

Also removed from concentrator 112 as a bottoms stream in line 116 is a cleavage feed rich in cyclohexyl-1-phenyl-1-hydroperoxide, phenylcyclohexanols, if any, and components of lower volatility than phenylcyclohexanols. The cleavage feed may contain greater than 40 wt % and no greater than 95 wt % cyclohexyl-1-phenyl-1-hydroperoxide. The cleavage feed in line 116 also includes a low amount of cyclohexylbenzene and components of a higher volatility than cyclohexylbenzene, for example, water. For example, the cleavage feed may comprise at least 5.0 wt % but less than 60 wt %, for example no greater than 40 wt %, or even no greater than 25 wt %, cyclohexylbenzene, and no greater than 1000 wppm, such as no greater than 100 wppm, or even no greater than 10 wppm water.

The cleavage feed is fed by line 116 to a cleavage reactor 126, which also receives sulfuric acid via line 118 and water via line 120. Alternatively, not shown in FIG. 1, sulfuric acid and/or water may be mixed with the cleavage feed in line 116, and that mixture provided to cleavage reactor 126. Conditions in cleavage reactor 126 are such that a cleavage reaction takes place, causing the cyclohexyl-1-phenyl-1-hydroperoxide, and also any other hydroperoxides and dihydroperoxide present, to decompose to materials including phenol and cyclohexanone, and producing 1-phenylcyclohexanol, e.g., as a byproduct of the cleavage of cyclohexyl-1-phenyl-1-hydroperoxide, and secondary phenylcyclohexanols from the decomposition of hydroperoxides other than cyclohexyl-1-phenyl-1-hydroperoxide. A cleavage product including phenol, cyclohexanone, cyclohexylbenzene, water, sulfuric acid, and 1-phenylcyclohexanol is withdrawn from cleavage reactor 126 in line 130.

The cleavage product in line 130 also may contain at least some of the oxidation catalyst and is mixed with a base, conveniently a relatively high molecular weight amine, for example, 2-methylpentane-1,5-diamine, supplied via line 132. The base complexes with and neutralizes the sulfuric acid in the cleavage product in line 130, creating a neutralized cleavage product in line 134. The neutralized cleavage product in line 134 thus now comprises phenol, cyclohexanone, 1-phenylcyclohexanol, optionally NHPI, and an acid-base complexation product that is an amine-sulfuric acid salt(s). Conveniently, the salt is completely soluble in the balance of the neutralized cleavage product and further may have a relatively low volatility compared to cyclohexylbenzene.

The neutralized cleavage product in line 134 is directed to a separation device, for example, fractionation column 136. Fractionation column 136 is operated to remove a second overhead product from the neutralized cleavage product by way of line 134. The second overhead product in line 138 is rich in phenol, cyclohexanone and components of a lower volatility than phenol, and includes a low amount of cyclohexylbenzene, for example, no greater than 5.0 wt %, or no greater than 2.0 wt %, or no greater than 0.1 wt % cyclohexylbenzene. Fractionation column 136 is further operated to produce a bottoms product, which exits the fractionation column 136 in line 140 and is rich in cyclohexylbenzene, phenylcyclohexene, phenylcyclohexanols, if any, and components of lower volatility than phenylcyclohexanols. The bottoms product in line 140 includes a low amount of light components, for example, water, pentanal, hexanal, methylcyclopentanone, cyclohexanone and phenol, comprising no greater than 1.0 wt %, or no greater than 0.1 wt %, or even no greater than 100 wppm of water, pentanal, hexanal, methylcyclopentanone, cyclohexanone, and phenol combined.

The operating conditions within fractionation column 136 include a point having a temperature of greater than 70° C. to which 1-phenylcyclohexanol will be exposed such that at least a portion of 1-phenylcyclohexanol is thermally dehydrated to phenylcyclohexene. As noted above, the phenylcyclohexene and any unreacted 1-phenylcyclohexanol exit fractionation column 136 in the bottoms product in line 140. Along with phenylcyclohexene, water may also be produced in fractionation column 136 as a co-product of the dehydration of 1-phenylcyclohexanol. Fractionation column 136 may be fitted with means, not shown in FIG. 1, to properly manage the production of water, e.g. a water boot in a condenser drum on the overhead product circuit with a separate line for withdrawal. The phenylcyclohexene produced may undergo additional processing to be made suitable for eventual recycle to oxidation reactor 106, including additional separation operations to remove low volatility heteroatom and oxygenated components that may be present in the neutralized cleavage product in line 134, and hydrogenation to cyclohexylbenzene, conveniently as a mixture with unreacted cyclohexylbenzene or fresh cyclohexylbenzene, or both.

Figure 2:
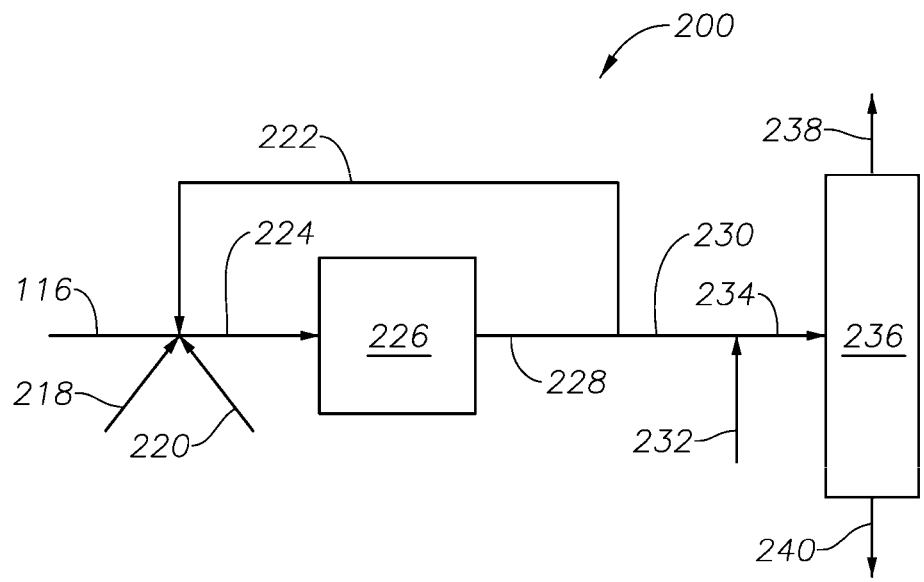
FIG. 2 is a flow diagram of a portion of a process for producing phenol and/or cyclohexanone according to a second example of the present application.

Referring now to FIG. 2, the exemplary process employs the same oxidation step as the process shown in FIG. 1 to produce a cleavage feed containing greater than 40 wt % and no greater than 95 wt % cyclohexyl-1-phenyl-1-hydroperoxide, and at least 5.0 wt % and less than 60 wt % cyclohexylbenzene. The cleavage feed is supplied by line 116 and is mixed with a cleavage recycle in line 222 to provide a cleavage reaction mixture in line 224. The cleavage recycle in line 222 contains phenol, cyclohexanone, cyclohexyl-1-phenyl-1-hydroperoxide, cyclohexylbenzene, water and sulfuric acid. The cleavage reaction mixture in line 224 contains at least 20 wt % and no greater than 50 wt % phenol, at least 20 wt % and no greater than 50 wt % cyclohexanone, at least 1.0 wt % and no greater than 10.0 wt % cyclohexyl-1-phenyl-1-hydroperoxide, at least 5.0 wt % and no greater than 60 wt % cyclohexylbenzene, at least 0.1 wt % and no greater than 4.0 wt % water, and at least 10 wppm and no greater than 1000 wppm sulfuric acid.

Make-up sulfuric acid in line 218 and make-up water in line 220 may be provided along with the cleavage feed in line 116 and the cleavage recycle in line 222, to provide the cleavage reaction mixture in line 224 possessing the desired composition. Alternatively, not shown in FIG. 2, make-up sulfuric acid and/or make-up water may be added to the cleavage feed in line 116, and the result of that addition mixed with the cleavage recycle in line 222 to form the cleavage reaction mixture in line 224 possessing the desired composition. In another alternative not shown in FIG. 2, make-up sulfuric acid and/or make-up water may be added to the cleavage recycle in line 222, and the result of that addition mixed with the cleavage feed in line 116 to provide the cleavage reaction mixture in line 224 possessing the desired composition. Such make-up sulfuric acid and make-up water may be provided at any manner to account for the loss or gain of those components from the cleavage reactor circuit, involving the material in the cleavage feed in line 116, the cleavage recycle in line 222, the cleavage effluent in line 228, the cleavage product in line 230, and the reaction in cleavage reactor 226, in order to provide the desired composition of the cleavage reaction mixture in line 224.

The cleavage reaction mixture in line 224 is provided to a cleavage reactor 226 which is operated at a temperature of at least 30° C. and no greater than 70° C., and a pressure of at least 1 atmosphere. A cleavage reaction takes place in cleavage reactor 226, causing the cyclohexyl-1-phenyl-1-hydroperoxide, and also any other hydroperoxides and dihydroperoxide present in the cleavage reaction mixture, to decompose to materials including phenol and cyclohexanone. Conditions in cleavage reactor 226 may be also such that at least 50% of the cyclohexyl-1-phenyl-1-hydroperoxide present in the cleavage reaction mixture is converted in cleavage reactor 226. For example, essentially all of the cyclohexyl-1-phenyl-1-hydroperoxide present in the cleavage reaction mixture may be converted in cleavage reactor 226, such that, there is no detectable cyclohexyl-1-phenyl-1-hydroperoxide present in the cleavage effluent. The cleavage effluent exits the cleavage reactor 226 in line 228 and contains phenol, cyclohexanone, cyclohexylbenzene, water, sulfuric acid, and 1-phenylcyclohexanol.

The cleavage effluent in line 228 is divided into the aforementioned cleavage recycle in line 222 and a cleavage product in line 230, with the composition of the material in each of lines 228, 222 and 230 being the same. The rate of flow of the cleavage recycle in line 222 can be from about 20 to about 30 times the rate of flow of the cleavage product in line 230.

The cleavage product in line 230 is mixed with a base, conveniently a relatively high molecular weight amine, for example, 2-methylpentane-1,5-diamine, in line 232 to complex with and neutralize the sulfuric acid in the cleavage product and create a neutralized cleavage product in line 234. The neutralized cleavage product in line 234 thus now comprises phenol, cyclohexanone, 1-phenylcyclohexanol, optionally NHPI, and an acid-base complexation product that is an amine-sulfuric acid salt(s). Conveniently, the salt is completely soluble in the neutralized cleavage has a relatively low volatility compared to cyclohexylbenzene.

The neutralized cleavage product in line 234 is directed to a separation device, for example, fractionation column 236, which is operated to remove a second overhead product from the neutralized cleavage product in line 238. The second overhead product is rich in phenol, cyclohexanone and components of a lower volatility than phenol, and includes a low amount of cyclohexylbenzene, for example, no greater than 5.0 wt %, or no greater than 2.0 wt %, or no greater than 0.1 wt % cyclohexylbenzene. Fractionation column 236 is further operated to form a bottoms product that is removed in line 240. The bottoms product is rich in cyclohexylbenzene, phenylcyclohexene, phenylcyclohexanols, if any, and components of lower volatility than phenylcyclohexanols, and includes a low amount of light components, for example, water, pentanal, hexanal, methylcyclopentanone, cyclohexanone and phenol, comprising no greater than 1.0 wt %, or no greater than 0.1 wt %, or even no greater than 100 wppm of water, pentanal, hexanal, methylcyclopentanone, cyclohexanone, and phenol combined.

The operating conditions within fractionation column 236 include a point having a temperature of greater than 70° C. to which 1-phenylcyclohexanol will be exposed, and conversion of 1-phenylcyclohexanol will take place, mainly to phenylcyclohexene. As noted above, the bulk of the phenylcyclohexene and any unreacted 1-phenylcyclohexanol exit fractionation column 236 in the bottoms product in line 240. Along with phenylcyclohexene, water may also be produced in fractionation column 236 as a co-product of the dehydration of 1-phenylcyclohexanol. Fractionation column 236 may therefore be fitted with means, not shown in FIG. 2, to properly manage the production of water, e.g., a water boot in a condenser drum on the overhead product circuit with a separate line for withdrawal. The phenylcyclohexene produced may undergo additional processing to be made suitable for eventual recycle to an oxidation reactor, including additional separation operations to remove low volatility heteroatom and oxygenated components that may be present in the neutralized cleavage product in line 234, and hydrogenation to cyclohexylbenzene, conveniently as a mixture with unreacted cyclohexylbenzene or fresh cyclohexylbenzene, or both.

The invention claimed is:

1. A process for producing phenol and/or cyclohexanone, the process comprising:
    (a) providing a cleavage reaction mixture containing cyclohexyl-1-phenyl-hydroperoxide and cyclohexylbenzene;
    (b) contacting at least a portion of the cleavage reaction mixture with sulfuric acid and water under cleavage conditions effective to form a cleavage reaction effluent containing phenol, cyclohexanone, cyclohexylbenzene, water, sulfuric acid, and 1-phenylcyclohexanol;

(c) neutralizing at least a portion of the cleavage reaction effluent with a basic material to produce a neutralized cleavage product; and (d) supplying at least a portion of the neutralized cleavage product in the absence of an added dehydration catalyst to a distillation column which is operated so that at least a portion of the neutralized cleavage product is exposed to a temperature within the range from 80° C. to 120° C. at at least one location in the distillation column whereby at least a portion of the 1-phenylcyclohexanol in the neutralized cleavage product is dehydrated to phenylcyclohexene.

2. The process of claim 1, wherein the cleavage reaction mixture contains from 1.0 wt % to 10 wt % cyclohexyl-1-phenyl-hydroperoxide and from 5.0 wt % to less than 60 wt % cyclohexylbenzene.

3. The process of claim 1, wherein the cleavage reaction mixture also contains phenol and cyclohexanone recycled from the cleavage reaction effluent.

4. The process of claim 1, wherein in step (c), the neutralized cleavage product comprises no more than 50 ppm by weight of sulfuric acid and no more than 50 ppm by weight of the basic material.

5. The process of claim 1, wherein the cleavage conditions include a temperature no greater than 70° C.

6. The process of claim 1, wherein the cleavage conditions include a temperature in a range from 30° C. to 70° C.

7. The process of claim 1, wherein the distillation column is a dividing wall distillation column.

8. The process of claim 1, wherein the distillation column produces at least one overhead stream containing phenol and cyclohexanone and less than 5.0 wt % of cyclohexylbenzene and at least one stream containing cyclohexylbenzene and phenylcyclohexene and less than 1.0 wt % of phenol and cyclohexanone combined.

9. A process for producing phenol and/or cyclohexanone, the process comprising:

(a) providing a cleavage feed containing greater than 40 wt % and no greater than 95 wt % cyclohexyl-1-phenyl-hydroperoxide and at least 5.0 wt % and less than 60 wt % cyclohexylbenzene;

(b) mixing the cleavage feed with a cleavage recycle containing phenol, cyclohexanone, cyclohexylbenzene, water, and sulfuric acid, to produce a cleavage reaction mixture containing from 20 wt % to 50 wt % phenol, from 20 wt % to 50 wt % cyclohexanone, from 1.0 wt % to 10 wt % cyclohexyl-1-phenyl-hydroperoxide, from 5.0 wt % to 60 wt % cyclohexylbenzene, from 0.1 wt % to 4 wt % water, and from 10 wppm to 1000 wppm sulfuric acid;

(c) reacting at least a portion of the cleavage reaction mixture at a temperature from 30° C. to 70° C. for a time sufficient to convert at least 50% of the cyclohexyl-1-phenyl-hydroperoxide in the cleavage reaction mixture and produce a cleavage effluent containing phenol, cyclohexanone, cyclohexylbenzene, water, sulfuric acid, and 1-phenylcyclohexanol;

(d) dividing the cleavage reaction effluent into at least a cleavage product and the cleavage recycle;

(e) neutralizing at least a portion of the cleavage product with a basic material to produce a neutralized cleavage product; and (f) supplying at least a portion of the neutralized cleavage product in the absence of an added dehydration catalyst to a distillation column which is operated so that at least a portion of the neutralized cleavage product is exposed to a temperature within the range from 80° C. to 120° C. at at least one location in the distillation column whereby at least a portion of the 1-phenylcyclohexanol in the neutralized cleavage product is dehydrated to phenylcyclohexene.

10. The process of claim 9, wherein the weight ratio of the cleavage recycle to the cleavage product is from 1:1 to 50:1.

11. The process of claim 9, wherein the weight ratio of the cleavage recycle to the cleavage product is from 10:1 to 40:1.

12. The process of claim 9, wherein step (c) is conducted at a pressure of at least 1 atmosphere.

13. The process of claim 9, wherein in step (e), the neutralized cleavage product contains no more than 150 pm by weight of sulfuric acid and no more than 150 ppm by weight of the basic material.

14. The process of claim 9, wherein in step (e), the neutralized cleavage product contains no more than 50 ppm by weight of sulfuric acid and no more than 50 ppm by weight of the basic material.

15. The process of claim 9, wherein the distillation column is a dividing wall distillation column.

16. The process of claim 9, wherein the distillation column produces at least one overhead stream containing phenol and cyclohexanone and less than 5.0 wt % of cyclohexylbenzene and at least one bottoms stream containing cyclohexylbenzene and phenylcyclohexene and less than 1.0 wt % of phenol and cyclohexanone combined.

17. The process of claim 9, further comprising:

(g) contacting cyclohexylbenzene with an oxygen-containing compound in the presence of a catalyst under conditions effective to produce an oxidation product comprising cyclohexyl-1-phenyl-hydroperoxide and at least 70 wt % unreacted cyclohexylbenzene; and (h) removing at least a portion of the unreacted cyclohexylbenzene from the oxidation product to provide the cleavage feed.

18. The process of claim 17, wherein the catalyst comprises a cyclic imide.

19. The process of claim 17, wherein the cyclohexylbenzene is produced by alkylation of benzene with cyclohexene.

20. The process of claim 17, wherein the cyclohexylbenzene is produced by a reaction of benzene with hydrogen in the presence of a hydroalkylation catalyst.

21. The process of claim 20, wherein the hydroalkylation catalyst comprises a solid acid alkylation component and a hydrogenating metal component.

22. The process of claim 21, wherein the solid acid alkylation component comprises a molecular sieve.

23. The process of claim 21, wherein the solid acid alkylation component comprises a molecular sieve of the MCM-22 family.

* * * * *